US009788798B2

(12) United States Patent
Van Ooijen et al.

(10) Patent No.: US 9,788,798 B2
(45) Date of Patent: Oct. 17, 2017

(54) METHOD OF VISUALIZING A BRIDGE THERAPY PROCESS

(75) Inventors: Henk Jan Van Ooijen, Wijk en Aalburg (NL); Rene Van Den Ham, Utrecht (NL); Bart Bakker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 191 days.

(21) Appl. No.: 14/126,545

(22) PCT Filed: Jun. 12, 2012

(86) PCT No.: PCT/IB2012/052961
§ 371 (c)(1),
(2), (4) Date: Dec. 16, 2013

(87) PCT Pub. No.: WO2012/172481
PCT Pub. Date: Dec. 20, 2012

(65) Prior Publication Data
US 2014/0118356 A1    May 1, 2014

(30) Foreign Application Priority Data

Jun. 16, 2011   (EP) ..................................... 11170089

(51) Int. Cl.
*G06T 11/20* (2006.01)
*A61B 5/00* (2006.01)
(Continued)

(52) U.S. Cl.
CPC ............ *A61B 5/7275* (2013.01); *A61B 5/026* (2013.01); *A61B 5/02028* (2013.01);
(Continued)

(58) Field of Classification Search
None
See application file for complete search history.

(56) References Cited

U.S. PATENT DOCUMENTS

| 5,822,715 A | 10/1998 | Worthington et al. |
| 6,321,164 B1 * | 11/2001 | Braun ................ G01N 33/4905 |
| | | 702/22 |

(Continued)

FOREIGN PATENT DOCUMENTS

| CN | 101563693 A | 10/2009 |
| WO | 0193762 A2 | 12/2001 |

(Continued)

OTHER PUBLICATIONS

Pohl, B. et al. "The Quick Machine—A Mathematical Model for the Extrinsic Activation of Coagulation". Haemostasis, Basel, CH. vol. 24 1994, pp. 325-337.

(Continued)

*Primary Examiner* — Yingchun He

(57) ABSTRACT

The present invention provides for a simultaneous graphical representation, a risk of bleeding and a risk of thrombosis providing a visualized bridge therapy process. Furthermore, the present invention provides for a computer-based prediction of the haemostatic situation of the examined blood circulation by using a combination of a biochemical model and a pharmacokinetic model for calculation or another mathematical representation of the blood circulation.

16 Claims, 6 Drawing Sheets

(51) Int. Cl.
  *G06F 19/26* (2011.01)
  *G06F 19/00* (2011.01)
  *A61B 5/026* (2006.01)
  *A61B 5/02* (2006.01)

(52) U.S. Cl.
  CPC .......... *A61B 5/4848* (2013.01); *A61B 5/7278* (2013.01); *A61B 5/742* (2013.01); *A61B 5/7475* (2013.01); *G06F 19/26* (2013.01); *G06F 19/345* (2013.01); *G06F 19/3437* (2013.01); *G06F 19/3456* (2013.01)

(56) References Cited

U.S. PATENT DOCUMENTS

| | | | |
|---|---|---|---|
| 6,524,861 | B1 | 2/2003 | Anderson |
| 6,730,026 | B2 | 5/2004 | Christ et al. |
| 6,890,299 | B2 | 5/2005 | Cohen et al. |
| 8,630,808 | B2 | 1/2014 | Kurkin et al. |
| 9,110,062 | B2 | 8/2015 | Gurbel |
| 9,513,301 | B2 | 12/2016 | Bergmann et al. |
| 9,539,218 | B2 | 1/2017 | Misselwitz et al. |
| 2004/0044272 | A1 | 3/2004 | Moerman et al. |
| 2004/0167763 | A1 | 8/2004 | Liebman |
| 2005/0074803 | A1* | 4/2005 | Schmitt ............ G06Q 50/24 435/6.16 |
| 2006/0015261 | A1 | 1/2006 | Mann et al. |
| 2006/0281140 | A1* | 12/2006 | Ranby ............... G01N 33/86 435/13 |
| 2009/0233312 | A1 | 9/2009 | Gibbons et al. |
| 2009/0265182 | A1 | 10/2009 | Peterson et al. |
| 2009/0298103 | A1 | 12/2009 | Mann et al. |
| 2011/0040572 | A1 | 2/2011 | Chmiel et al. |
| 2012/0166222 | A1* | 6/2012 | Howard ............ G06Q 50/24 705/3 |
| 2014/0118356 | A1 | 5/2014 | Van Ooijen et al. |

FOREIGN PATENT DOCUMENTS

| | | |
|---|---|---|
| WO | 03014735 A1 | 2/2003 |
| WO | 2010124127 A1 | 10/2010 |

OTHER PUBLICATIONS

Rodriguez-Fernandez, M. et al., "Global Sensitivity Analysis of a Biochemical Pathway Model." 2nd International Workshop on Practical Applications of Computational Biology and Bioinforrnatics, vol. 49, pp. 233-242, Abstract.

Ganter, M.T. et al., "Coagulation Monitoring: Current Techniques and Clinical Use of Viscoelastic Point-of-Care Coagulation Devices", Anesthesia & Analgesia, vol. 106, Nr: 5, pp. 1366-1375.

Ganter, M.T. et al., "Point of Care coagulation Monitoring", Chapter Monitoring Technologies in Acute Care Environments, pp. 329-342, 2014, Abstract.

Enriquez, L.J. et al., "Point of care coagulation testing and transfusion algorithms", British Journal of Anaesthesia, vol. 103, Nr: supplement 1, pp. 114-122.

Beringer, P.B. et al., "The Quick Machine—A Mathematical Model for the Extrinsic Activation of Coagulation," Haemostasis, vol. 24, pp. 325-337, Abstract.

Frey, H.C. et al, "identification and Review of Sensitivity Analysis Methods", Risk Anal, (2002), vol, 22, No. 3, pp. 553-578.

Kucher, N. et al., "Electronic Alerts to Prevent Venous Thromboernbolism Among Hospitlized Patients", The New England Journal of Medicine, Mar. 10, 2005, vol. 352, No. 10 pp. 969-977.

Stammers, A.H. et al., "Point of Care Coagulation monitoring: applications of the thromboelastograph", Anaesthetists, 1998, Supp 2, pp. 58-59.

* cited by examiner

METHOD OF VISUALIZING A BRIDGE THERAPY PROCESS

This application is a national stage application under 35 U.S.C. §371 of International Application No. PCT/IB2012/052961 filed on Jun. 12, 2012 and published in the English language on Dec. 20, 2012 as International Publication No. WO/2012/172481, which claims priority to European Application No. 11170089.4 filed on Jun. 16, 2011, the entire disclosures of which are incorporated herein by reference.

FIELD OF THE INVENTION

The present invention relates to clinical decision support systems. In detail, the present invention relates to a method of visualizing a bridge therapy process, to a user interface for visualizing a bridge therapy process, to a program element for visualizing a bridge therapy process and a computer readable medium.

BACKGROUND OF THE INVENTION

Medicinal anti-coagulation therapy has the risk of causing life-threatening bleeding events. Therefore, anti-coagulation therapy is regularly monitored to obtain the right balance between thrombosis and bleeding risk. The diagnostic test that is best used for this purpose depends on the type of anticoagulant drug that is administered. For short term anti-coagulation therapy that needs fast adjustments, unfractionated heparin, or heparin-like drugs such as low-molecular weight heparin (LMWH) and pentasaccharides are used. For longer term therapy, oral, vitamin K antagonist (VKA) type anticoagulants are most widely used. Approximately 1 to 2 out of every 100 people living in the western world uses VKAs.

VKA and heparin-like compounds have different modes of action. Heparin increases the function of anti-thrombin to inhibit mainly both F10a and thrombin. Heparin also inhibits also other active proteins such as F11a, F9a, F3-F7a, however their main mode of action is inhibition of F10a and thrombin. LMWH and the synthetic pentasaccharides may be more specific to F10a. The VKAs may inhibit the concentrations of functional thrombin, F7, F9, F10 protein C, protein S and protein Z. The most used test for heparin therapy is the activated partial thromboplastin time (aPTT), while the anti-Factor 10a assay is generally used to monitor LMWH or synthetic pentasaccharide type of drugs. Vitamin K antagonist therapy is traditionally monitored using the prothrombin time (PT), or its standardized derivative, the international normalized ratio (INR).

During certain situations however, for example after the acute phase of thrombosis treatment, or when a patient on vitamin K antagonists needs to undergo surgery, the therapy needs to change from one type of drug to another, also known as bridge or bridging therapy. Annually an estimated total of 250.000 patients need interruption of their VKA treatment in North America alone. This does not take into account all patients that start Warfarin treatment after an initial treatment with heparin. It is estimated that about 2 mln persons start Warfarin treatment each year. However, not all of these patients may have had an initial heparin treatment.

The action of VKA only slowly increases (transition from heparin-like drug to VKA) and also only decreases slowly (transition from VKA to heparin-like drug) due to an indirect effect on the production of the coagulation proteins.

There is not a test available that encapsulates the combined effect of both therapies. Furthermore, the tests used to measure the effect of a single therapy, e.g. aPTT or INR, are affected by the other therapy. VKA action only slowly increases and decreases due to its indirect effect on the coagulation proteins, and during this therapy, their partial anti-coagulation needs to be compensated for by the fast-acting heparin-like drugs to keep the patient in the correct hemostatic balance.

The physician has several options to monitor the hemostatic balance of the patient during the bridging period. First, the PT or INR can be used to monitor the patient during the bridging period. However, since the PT/INR is relatively insensitive to the effects of the heparin like drugs, targeting a constant value for this test will easily lead to overcompensation of the coagulation and an unacceptable high risk of bleeding. Similarly for the second option, using the aPTT to monitor the anti-coagulation, the aPTT is somewhat sensitive to the anti-coagulant effect of the VKAs but is certainly not optimized to monitor VKA therapy, thus targeting a constant value for this test will also easily lead to over-anti-coagulation and an unacceptable high risk of bleeding. In practice, physicians are known to opt for the third possibility: refrain from monitoring at all, but follow the (recommended) bridging guidelines, which are known to often lead to over-anti-coagulation.

SUMMARY OF THE INVENTION

It might be seen as an object of the present invention to provide for an improved bridging therapy.

There may be a need to intuitively visualize a bridge therapy process of a patient and indicate whether the provided anti-coagulation is out of the intended safe range. In addition, there might be a need to collect relevant patient data and there might be a need to provide for linked recommendations to e.g. clinician or user for a safe bridge process. Consequently, there might be a need to enable a user to correctly monitor and to safely compensate for a partial anti-coagulation of a patient.

The present invention matches these needs.

The object of the present invention is solved by the subject-matter of the independent claims. Further embodiments and further advantages are incorporated in the dependent claims.

It should be noted that the embodiments of the invention described in the following similarly pertain to the method, to the device, to the program element as well as to the computer-readable medium. In other words, features that will be described with regard to the embodiments relating to a method of the present invention shall be understood to be comprised or implemented by the corresponding device, the program element and the computer-readable medium of the present invention, and vice versa. Furthermore, a person skilled in the art will gather from the above and the following description that, unless otherwise notified, in addition to any combination belonging to one type of subject-matter, also any combination between features relating to different subject-matters, in particular between features of the apparatus type claims and features of the method type claims, is considered to be disclosed with this application. Furthermore, all features can be combined providing synergetic effects that are more than the simple summation of the features.

According to an exemplary embodiment of the invention, a method of visualizing a bridge therapy process or a bridging therapy process is presented. The method comprises the steps of receiving coagulation data describing a haemostatic situation of a blood circulation of a patient. Furthermore, the method comprises the step of displaying the coagulation data to a user by means of a graphical representation which is a graphical representation. The step displaying a first measured value of a first type of blood test in said graphical representation is further comprised, wherein the first measured value indicates a first effect of a heparin-like drug on the haemostatic situation. Simultaneously to said displaying of said first measured value, a second measured value of a second type of blood test is displayed in said graphical representation, i.e. at the same point in time. The second measured value indicates a second effect of a vitamin K antagonist-type anticoagulant on the haemostatic situation, wherein the first and second measured values describe the haemostatic situation of the blood circulation at one i.e. at the same specific point in time.

As both types of blood tests are performed at essentially the same point in time, reliable information about the haemostatic situation of the patient, at said specific point in time is possible.

In the above described embodiment and in every other embodiment of the invention the results of the first and second type of blood tests may be measured but may also be computer generated. As will be described below in detail, a mathematical model might be used in the context of the present invention which takes into account biochemical aspects or characteristics and pharmacodynamical aspects or characteristics of the examined or monitored haemostatic situation of the blood and pharmacokinetical aspects or characteristics of the examined or monitored haemostatic situation of the blood. This may also include patient characteristics such as genetic variations, etc.

In other words the method of visualizing a bridge therapy process may also be completely based on simulated values of a first and second type of blood tests. However, if desired, a combination of measured values taken from a blood sample and simulated, calculated or modeled values is comprised in the present invention. Moreover, also only measured values may be used to monitor the time progression of the values of the first and second blood tests.

Speaking generally the first and third effect may be of the same or essentially the same nature. However, they may be present in the examined blood at a different point in time and may represent another impact on the haemostatic potential or haemostatic situation of the patient.

Furthermore the "displaying" of the first and second measured value is performed in the graphical representation as described above and below. For example, a user interface may additionally be provided in a first step in order to provide for the graphical representation and to display the first and second measured values to a user.

In the context of the present invention the term "blood circulation" may be understood as the haemostatic situation of the blood circulation.

The first and second measured values may for example be X and Y coordinates in a coordinate system which is displayed in the graphical representation. In other words, the presented method simultaneously displays a risk of coagulation and a risk of bleeding of said haemostatic situation of the blood circulation by means of the first and second measured value. Such a simultaneously displaying may for example be gathered from FIG. 6 which is described hereinafter. In other words one test indicates a risk of thrombosis or a coagulation risk and the other test indicates risk of bleeding. Both tests may indicate either risk through test values that are either higher or lower than a safe or target range of potential test outputs.

Furthermore the simultaneous representation of the risk of bleeding and the risk of thrombosis of the examined blood circulation by means of the first and second measured values of different types of blood tests and the advantages thereof will become clearer from the following example of the herein presented method. The first type of blood test might be for example a PT/INR test. This type of blood test might be relatively insensitive to the effects of heparin-like drugs. Due to the simultaneous displaying or monitoring according to the present invention, not only a safe range for this exemplary first type of blood test is targeted during bridging. Thus an overcompensation of the coagulation and an unacceptably high risk of bleeding is successfully avoided by the present invention, as simultaneously a second measured value of the second type of blood test is displayed and/or monitored. The second type of blood test might for example be embodied by an aPTT blood test. This test might be somewhat sensitive to the anticoagulant effect of the VKAs but may certainly not be optimized to monitor VKA therapy, but rather to monitor the effects of heparin-like drugs. As the present invention is not targeting a constant value of this aPTT during bridging, which is to be seen as the second type of blood test, it is avoided that an over anticoagulation and a high unacceptable risk of bleeding establishes during the monitored bridge process.

The method assists in keeping the patient at a safe hemostatic balance throughout the bridging period. For example, at the start of bridging from VKA to heparin the patient is stable within a target zone defined purely by PT/INR, at the finish of the bridging process the patient should be stable within a target zone for defined purely by aPTT. In between, the combination of the two tests indicate a safe transition zone in which the intermediate measurement values should remain.

Simultaneous visualization of these two measurements shows whether the patient is stable and may be useful by itself. There may be an innovative influence of the model, which predicts whether the patient will still be stable at the next point in time, based on measurements 1 and 2, additional patient specific data, as will be described later on, and changes in anticoagulant drug dosage. The latter part links clinical decisions in terms of drug administration to progress of a patient within or outside the safe area, and can thus be used to recommend correct or warn against dangerous drug dosage.

In other words the present invention targets to display measurements of the first blood test which are related to heparin like drugs and targets to simultaneously measurements of vitamin K antagonists type anticoagulant drugs, which increases the reliability and precision of the bridge therapy support provided by the present invention.

Therefore, the presented method enables a user to correctly monitor the bridge therapy and safely compensate for an insufficient or too much anti-coagulation. For example, by displaying results of PT test and by simultaneously displaying aPTT test results, a user might be enabled to estimate how the haemostatic situation of the analyzed blood circulation is evolving. An additional calculated suggestion may be provided to the user based on the first and second values of the first point in time, and possibly on additional measured values or time points further down the bridging period which are predicted by the mathematical model. For said suggestion the herein described mathematical model may be used. The model may well use such measured values in addition to PT/INR and aPTT, to make the model's contribution more reliable.

In the context of the present invention, the term "measured values" of a e.g. first type of blood test may be seen as a blood test which gives the user information about coagulation factors, anti-coagulation factors, factors influencing thrombosis, factors influencing bleeding or any parameter which has to be known by a clinician to assess the haemostatic situation. The term factor may be seen as a parameter or a value which entails significance about bleeding risk or a thrombosis risk of the examined blood circulation.

Such measured values may also be seen as results of e.g. clinical measurements. Such results of clinical measurements may be provided to a user interface which performs the simultaneous displaying of both first and second measured values of the respective type of blood test.

The presented method simultaneously displays to the user the effect of heparin-like drugs administered previously or intended to be administered on the haemostatic situation of the blood circulation. Simultaneously, the method displays the second effect of a vitamin K antagonist-type anticoagulant on the haemostatic situation of the analyzed blood circulation. Therefore, during the bridge therapy process the user is provided with an overview of the effects that are caused by unfractionated heparin and/or heparin-like drugs such as low molecular weight heparin and pentasaccharide as well as the effects that are caused by vitamin K antagonist type anticoagulants. Therefore, by the present invention bridging therapy processes may be improved with regard to their safety and with regard to the reliability of the blood tests performed during the bridge therapy process.

In the context of the invention first, second, third and fourth values may be seen as being comprised by the calculation data which is provided e.g. to a user interface, to a display, to a processor, to a computer system or as it is used in the presented method. Of course even more values may be seen as being comprised by the calculation data.

According to another exemplary embodiment of the invention, the method further comprises the step of displaying a third value of the first type of blood test, which third value indicates a third effect of a heparin-like drug on the haemostatic situation. Simultaneously to the displaying of the third value, a fourth measured value of a second type of blood test is displayed.

Therein the third and fourth value may be measured or also computer generated by e.g. an embodiment of the herein described mathematical model.

In other words, this exemplary embodiment can be exemplified by using an X and Y coordinate system. Consequently, this exemplary embodiment of the invention can be seen as displaying two different points of time in the X and Y coordinate system, wherein on the X axis for example aPTT values are displayed and on the Y axis INR values are displayed. Also other test described herein may be used. The first and second values, which might be measured previously, could be combined within a first X and Y coordinate and the third and fourth values, which might e.g. be measured, could be combined with a second X and Y coordinate. Hence, a measured or a predicted time progression or time progression based on measured start values and calculated values is generated and displayed by means of the first, second, third and fourth values. Thus a user is informed graphically how the haemostatic situation of the analyzed blood circulation has changed from the first X and Y coordinate to the second X and Y coordinate. The time progression of the haemostatic situation of said analyzed blood circulation may be displayed or represented in the graphical representation.

The above descried process can be continued also for a third point in time and so on until the bridging is finished.

It should be noted that in the context of the present invention the first and second type of blood tests may respectively and independently be chosen from the group consisting of activated partial thromboplastin time (aPTT) test, anti-Factor 10a test, prothrombin time (PT) test, international normalized ratio (INR) test, a test indicating thrombosis or coagulation, a test indicating bleeding or anticoagulation, a test indicating the haemostatic function or any test combination thereof.

According to another exemplary embodiment of the invention the method comprises the step of calculating and/or displaying a prediction of the haemostatic situation of the blood circulation by combining a biochemical model of the blood circulation and a pharmacodynamical model of the blood circulation.

In the context of the present invention, the terms "pharmacodynamical model" is used to comprise pharmacokinetical as well as pharmacodynamical aspects. Thus the mathematical model in the context of the present invention includes both pharmacodynamics, i.e. drug-protein interactions, and pharmacokinetics, i.e. the spreading of the drug through the system. The pharmacodynamical model may be based not only on distribution in the vessels but in the whole body. So it starts with absorbing the drug, than distribution of the drug occurs throughout the body also leading to a certain amount of drug in the blood circulation, and so on. The amount of drug in the blood may be a parameter important to the presented model.

Said biochemical model and said pharmacodynamical model might be part of a mathematical model as will be described in more detail.

Said mathematical model calculates or simulates a time development or time progression of the types of blood tests that are used i.e. a time development or time progression of the first value of the first type of blood test and the second value of the second type of blood test.

In other words, said exemplary embodiment may be seen as a computer-supported decision method. By means of the calculated predictions a user may decide which administration of drugs may be useful. The result of the prediction may be accompanied by a calculated suggestion of a change of administration of anticoagulation drugs.

Said calculation of the prediction may be performed e.g. on a computer or a processor of a computer. The used models, the biochemical model and the pharmacodynamical model may be stored on a storage device of a computer system or may also be downloaded as a part of a computer program element in order to update or adapt an existing program or system.

In the context of the present invention the biochemical model and the pharmacodynamical model may be seen as one mathematically defined model that may consist of three separate modules: a coagulation cascade module, a fibrin polymerization module and a pharmacokinetics and/or pharmacodynamics module. The first modules may be named as a biochemical model. The first two modules relating to coagulation cascade and fibrin polymerization, may be based on the underlying protein interactions of the coagulation response, and are used to simulate in vitro tests such as, but not limited to, the thrombin generation assay, prothrombin time (PT) and activated partial thromboplastine time (aPTT). The biochemical model may therefore comprise calculations about the coagulation cascade and calculations about the fibrin polymerization inside of the examined blood circulation or blood vessel system or body of the patient. The pharmacokinetics and pharmacodynamics may be based on compartment modeling. However, other numerical modeling may be used. If desired, finite element modeling may be used separately or additionally. The pharmacodynamical model may be used to simulate the kinetics and effect of the anticoagulant drugs such as, e.g. unfractioned heparin (UFH), low-molecular weight heparin (LMWH) and VKA in the human body. The term "blood circulation" may therefore be seen as part or the whole human body blood circulation system.

The following interaction between the biochemical model and the pharmacodynamical model may be implemented, if desired, in each embodiment of the present invention: Effects of the anticoagulant drugs may be simulated for a part or the whole bridging period in time. A snapshot may be taken at a predefined time point from the simulated effect of the anticoagulants. Such a simulation may be performed by means of e.g. compartment modeling. Also other models such as numerical models may be used. For example, finite element modeling may be at least partially used. The snapshot is taken of the disturbed situation in the blood circulation and symbolizes one or more tests related to the coagulation system of a blood sample taken from the examined blood circulation of the patient. The snapshot may then be used in the biochemical model as an input in order to calculate the coagulation cascade and the fibrin polymerization respectively or alternatively. More mathematical details and several embodiments of the mathematical model combining a biochemical model and a pharmacodynamical model can be gathered from the mathematical description set out below.

In this and every other exemplary embodiment the term "calculating" may be understood as running a model or performing a simulation with a model e.g. with the mathematical model described herein.

According to another exemplary embodiment of the invention, the method comprises the step of calculating an effect of an anticoagulant drug during a predetermined time by using the pharmacodynamical model, which results in a calculated pharmacodynamical effect. In other words, by using the pharmacodynamical model, distribution times and distribution rates of, e.g. anticoagulants within, as well as their anti- or pro-coagulant effects on the blood circulation under examination may be modeled and/or calculated. Therein compartment modeling may be used in order to specify the dynamics of the drugs within the blood circulation and other tissues under examination.

Thereby it is of importance that the presented method for performing the modeling does not require any contact with the patient, as it may be based purely on a mathematical model. If desired, individual information about the patient or the blood system can be taken into account during the modeling, simulating or calculating steps of the presented method.

Said calculated pharmacodynamical effect may be used afterwards for the biochemical model, which may comprise calculation about the coagulation cascade of the examined blood circulation and calculations about fibrin polymerization of the examined blood circulation. This is also described by the tables 1 to 5 shown further down.

According to another exemplary embodiment of the invention, the method further comprises the steps of calculating a coagulation effect and/or a fibrin polymerization effect in all of the examined blood circulations by means of the biochemical model, wherein said calculation is based on the calculated pharmacodynamical effect.

In other words, relationship or interaction between the biochemical model and the pharmacodynamical model is presented. The user profits from the combination of the quite different mathematical models, as the advantages of the results of both models are combined, as will be described below.

The further step of displaying a prediction value of the haemostatic situation may also be comprised in the present exemplary embodiment. Therein the prediction value is based on at least one of the calculated pharmacodynamical effects, the calculated coagulation effects and/or the calculated fibrin polymerization effect.

In other words, the combination of the biochemical model and the pharmacodynamical model enables the user to adjust the bridging therapy based on the results of the previously performed calculation steps. The results of the combined simulations may be depicted on a display such that information about whether the haemostatic situation of the patient is safe is clearly displayed to the user. If desired, a graphical representation as shown in FIG. 6 may be used. Known boundary values for e.g. aPTT values and INR values which delimit the safe region may be displayed by means of e.g. a rectangular field. Such a rectangular field within the X and Y coordinate system indicates the region in which the aPTT and INR values need to be in order to meet safety requirements with regard to bleeding and/or thrombosis.

According to another exemplary embodiment the method comprises the step of automatically suggesting an application for administration of a coagulant and/or an anti-coagulant.

In other words, a model or software may be provided which supports a decision of a user or a clinician during a bridging therapy. Such an automatically generated suggestion may suggest e.g. an increase or decrease of UFH, the administration of VKA, the administration of procoagulants or coagulants, the administration of antidotes, or to keep the current therapy plan constant. However, other embodiments of suggestions that are automatically generated by the above-described model shall be understood to be comprised by the present invention.

Furthermore, the automatically suggested application is based on the previously calculated progression of the haemostatic situation. In other words, the combination of the biochemical model and the pharmacodynamical model may also comprise a step in which an optimal therapy plan during the bridging process is calculated and is displayed.

Furthermore, in this and every other embodiment of the present invention, the user may provide individual information about the patient or the blood circulation, which information can be classified into two types: A first type of individual data is constant in time and a second type of individual data may vary or change over time as bridging is progressing. As an example for said first data type, the name, blood group and or the bridging type may be provided. Examples for individual data about the blood circulation or the patient which may vary in time are e.g. INR value, an aPTT value, F2 activity and/or F10 activity.

As will be described later with regard to FIG. 5, a user interface may be a central device which is provided with clinical measurements, like e.g. INR values or aPTT values. Secondly, a user interface may be provided with user input about e.g. a possible or potential dosage of drugs which the clinician would like to assess by the model comprising a biochemical model and a pharmacodynamical model as described above. The user interface may therefore be in communication with a processor or software running system on which the mathematical models or calculations, as will be described below, can be read out or performed. In other words, the user interface may be connected to a calculation arrangement on which both models are stored and on which simulations can be performed using such models.

According to another aspect of the present invention the biochemical model and the pharmacodynamical model may be frequently updated through e.g. an IT system of a hospital through which current knowledge or scientific insights might be provided. Thus, the models are updated frequently and can be kept up to date.

According to another exemplary embodiment of the invention a user interface for visualizing a bridging therapy process is presented. The user interface comprises a receiving arrangement configured to receive coagulation data or other related clinical data describing a haemostatic situation of a blood circulation of a patient. Furthermore, the user interface is configured to display the haemostatic situation of said blood circulation. The user interface is further configured to display a first measured value of a first type of blood test, which first measured value indicates a first effect of a heparin-like drug on the haemostatic situation. Furthermore, the user interface is configured to simultaneously display a second measured value of a second type of blood test, which second measured value indicates a second effect of a vitamin K antagonist type anticoagulant on the haemostatic situation.

Furthermore, the first and second measured values describe the haemostatic situation of the blood circulation at one specific point in time.

It may be seen as a gist of the invention to simultaneously display to a user a risk of coagulation and a risk of bleeding of the examined blood circulation by means of only one graphical representation. This is done during a bridging therapy from one type of anticoagulant drug to another type of anticoagulant drug. In other words, in a first step a first measured value that is associated with the effects caused by heparin-like drugs is displayed in combination with a second value of a second test which is associated with effects caused by vitamin K antagonist type anticoagulant drugs in the examined blood circulation. Due to this simultaneous displaying step, it can be avoided that the haemostatic situation of the patient is an over-anticoagulation or under-anticoagulation. Due to this simultaneous displaying step, the development of over-anticoagulation or under-anticoagulation of the haemostatic situation can be avoided. Therefore, an improved bridging process is possible due to the present invention.

According to another exemplary embodiment of the invention a program element for visualizing a bridge therapy process or a bridging therapy process, which program element when being executed by a processor is adapted to carry out receiving coagulation data describing a haemostatic situation of a blood circulation, displaying the coagulation data to a user by means of a graphical representation, displaying a first measured value of a first type of blood test, which first measured value indicates a first effect of a heparin-like drug on the haemostatic situation, wherein the first measured value is displayed in said graphical representation. The program element may be further adapted to carry out simultaneously to the displaying of the first measured value a displaying of the second measured value of a second type of blood test, which second measured value indicates a second effect of a vitamin K antagonist type anticoagulant on the haemostatic situation.

Thereby, the term "program element" may be seen as a whole complete computer program or may also be seen as a part of a computer program. Such a part of a computer program might be downloaded and integrated into an already existing computer program as an update to be able to carry out the present invention.

According to another exemplary embodiment of the invention a computer readable medium in which a program element for visualizing a bridge therapy process is stored which, when being executed by a processor, is adapted to carry out receiving coagulation data describing a haemostatic situation of a blood circulation, displaying the coagulation data to a user by means of an graphical representation, displaying a first measured value of a first type of blood test, which first measured value indicates a first effect of a heparin-like drug on the haemostatic situation. The program element stored in the computer reader medium may be further adapted to carry out simultaneously to the displaying of the first measured value the displaying of a second measured value of a second type of blood test, which second measured value indicates a second effect of a vitamin K antagonist type anticoagulant on the haemostatic situation.

The computer readable medium may be seen as a storage medium, such as for example, a USB stick, a CD, a DVD, a data storage device, a hard disk, or any other medium on which a program element as described above can be stored.

These and other aspects of the invention will become apparent from and elucidated with reference to the embodiments described hereinafter.

It may be seen as a further gist of the invention to provide for a user interface, software, computer model, clinical measurements and characteristics of the patient (e.g. aPTT, INR, single-nucleotide polymorphism (SNP), coagulation factor activities, liver function). Especially the computer model may be based upon new understandings. It is a computer implementation of the human hemostatic system which was developed. This computer model can predict the future evolution of the patient's hemostatic system during bridge therapy based on measurements of the present.

The gist of the invention is described with different words in the following. The computer model may be a representation of the coagulation cascade and fibrin polymerization as a set of reaction mechanisms. The time dynamics of each reaction mechanism may be described as an ordinary differential equation or ODE that involves the concentration(s) of the protein(s) and/or chemical molecule(s) that are involved in the reaction and the reaction rate parameter(s). By summation of all reaction mechanisms in which a particular protein or other kind of chemical molecular is involved (a protein or molecule can participate in more than one reaction), the time dynamics of the concentration of that particular protein or other kind of chemical entity may be calculated. The whole system can be calculated by keeping track of the evolution of all proteins and molecules. This requires however that, beside the reaction topology, the numerical values of the model parameters are known as well. These model parameters include the initial conditions of the system, i.e. the concentration of all proteins and molecules at t=0 (e.g. before onset of bridging therapy), and the reaction rate parameters of the reaction mechanisms. Part of the initial concentrations are measured (in the laboratory or clinic), whereas others are taken from literature (average patient values, possibly corrected for gender and age). The reaction rate parameters may be derived via solving an inverse problem, i.e. model fitting to experimental data. The system of ODEs is solved numerically, using the numerical values of the model parameters, by employing standard ODE integration algorithms. The expected future evolution of the aPTT and INR, as predicted by the computer model, are shown on the UI together with the evolution of the measured aPTT and INR during the bridging period, which are/were entered in the UI by the user. The aPTT and INR-predictions are calculated by the computer model based on the initial concentrations that are determined in the tests, prederived reaction rate parameters and population average values for the unknown concentrations. The previously measured aPTT and INR values in combination with other clinical measurements, such as e.g. the activity of the vitamin K proteins, liver function, are used to optimize the predictions to be more patient specific, i.e. personalized therapy planning. The progression of the measured and predicted aPTT and INR during the bridging period is referred to as bridging path. The user can use the combined measured and predicted bridging path to assess the patient's risk and make appropriate adaptations to the therapy plan. The different therapy options can be simulated by the computer model and the predicted effects thereof are visualized on the UI.

BRIEF DESCRIPTION OF THE DRAWINGS

Exemplary embodiments of the description will be described in the following drawings:

FIGS. 1 to 3c schematically show a respective flow diagram of a method according to exemplary embodiments of the invention.

DETAILED DESCRIPTION OF EMBODIMENTS

Figure 1:
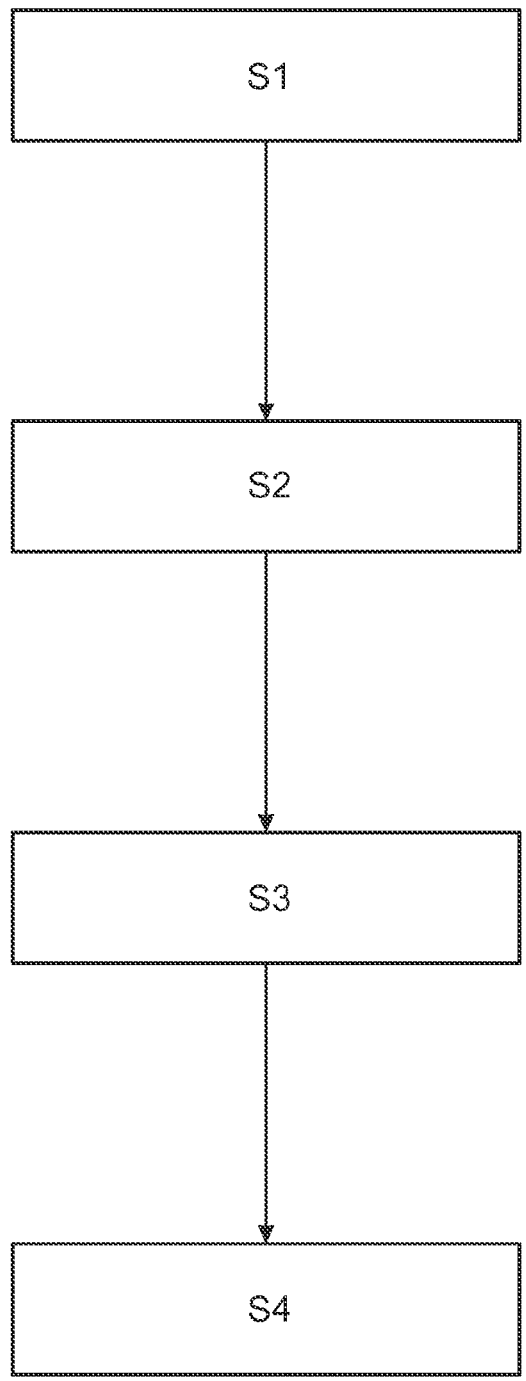

FIG. 1 shows a flow diagram of a method of visualizing a bridge therapy process wherein the presented method comprises steps (S1) to (S4). In step (S1) coagulation data describing haemostatic situation of a blood circulation of a patient is received. Such data may for example be received by a user interface or by a calculation arrangement or a computer system. Furthermore, the coagulation data comprise measured or simulated values of tests that indicate the haemostatic situation of a blood circulation. Therein values of an aPTT test, a PT test, an INR test, a test indicating thrombosis or coagulation, a test indicating bleeding or anticoagulation, a test indicating the haemostatic function and any test combination thereof, may be comprised by said term "coagulation data".

Furthermore, the method depicted in FIG. 1 comprises the step (S2) which represents a displaying of the coagulation data to a user by means of a graphical representation. Furthermore, the step of displaying a first measured or simulated value of a first type of blood test which first measured or simulated values indicates a first effect of a heparin-like drug on the haemostatic situation is comprised as step (S3) by the method of FIG. 1. Furthermore, step (S4) is comprised which is the step of simultaneously displaying a second measured or simulated value of a second type of blood test to the displaying of the first measured value. The second measured or simulated value indicates a second effect of a vitamin K antagonist type anticoagulant on the haemostatic situation. Furthermore, the first and second measured or simulated values describe a haemostatic situation of the blood circulation at one specific point in time.

Due to the simultaneous display of first and second values which originate from blood tests both effects caused by heparin-like drugs and effects caused by vitamin K antagonist type anticoagulant drugs can be monitored and are displayed to a user. Therefore, it is ensured that the balance between thrombosis and bleeding risk is detected by the clinician supported by this method of visualizing a bridging therapy process.

The first type of blood test might be a PT/INR test which might be relatively insensitive to the effects of the heparin-like drugs but might be sensitive to monitor the effect of VKAs. As with the present invention, not only a constant value for this test is targeted during bridging, an overcompensation of the coagulation and an unacceptably high risk of bleeding is successfully avoided by the present invention. The second type of blood test might for example be embodied by an aPTT blood test, which might be somewhat sensitive to the anticoagulant effect of the VKAs but may certainly not be optimized to monitor VKA therapy but might be sensitive to monitor the effect of heparin like drugs. As the present invention is not targeting a constant value of this test during bridging, it is avoided that an over anticoagulation and a high unacceptable risk of bleeding establishes. The present invention may simultaneously target measurements of the first blood test which are related to vitamin K antagonists type anticoagulant drugs and simultaneously targets measurements of heparin like drugs by the second type of blood test, which increases the reliability and precision of the bridge therapy support provided by the present invention.

If desired, the first measured value may be depicted as a value of an X-axis of an X and Y coordinate system. The second measured value may be depicted as a value of a Y-axis of said X and Y coordinate system. This may be gathered from the following FIG. 6. The graphical representation used during said method may comprise a functionality in which the user is alerted if the analyzed and observed haemostatic situation is evolving into a risk of thrombosis or a risk of bleeding. The user might be alerted by means of an optical, an acoustical or an electrical signal.

Furthermore, the graphical representation used in the presented method may be adapted in such a way that a risk of coagulation and a risk of bleeding of said analyzed blood circulation is simultaneously depicted. In other words, the displaying steps of the method of FIG. 1, steps (S2), (S3) and (S4) may be understood to show a coagulation risk based on at least one measured parameter chosen from the group consisting of aPTT, anti-Factor 10a, PT, INR), a parameter indicating thrombosis or coagulation, a parameter indicating bleeding or anticoagulation, a parameter indicating haemostatic function and any combination thereof. Furthermore, the displaying steps may be seen as to display a risk of bleeding to a user based on at least one measured parameter chosen from the group consisting of activated partial thromboplastine time (aPTT) test, anti-Factor 10a test, prothrombin time (PT) test, international normalized ratio (INR) test, a test indicating thrombosis or coagulation, a test indicating bleeding or anti-coagulation, a test indicating haemostatic function and any test combination thereof.

As both types of blood tests are performed at essentially the same point in time, reliable information about the haemostatic situation of the patient, at said specific point in time is possible.

If desired, the presented method of FIG. 1 can be extended to again perform the steps in a second round at a second point in time. Afterwards, a time-resolved progression of the risk of coagulation of said blood circulation and the risk of bleeding of said blood circulation may be displayed in the graphical representation.

If desired, both described embodiments regarding FIG. 1 may also be extended by a step of entering a test value into a user interface by the user. This may allow a user to calculate on the basis of a used mathematical model which may comprise a biochemical model and a pharmacokinetic model, how, for example the bleeding risk or the thrombosis risk has evolved, or will evolve if the present bridging treatment is continued without change, since the last retrieval of first and second measured values.

Furthermore, the user may enter into a user interface a changed administration of, for example, a heparin-like drug a vitamin K antagonist-type anticoagulant in order to obtain a predicted calculated progression of the analyzed blood circulation of a patient with regard to the bleeding and thrombosis risk. Calculation of such a prediction might be based on a mathematical model comprising a biochemical model and a pharmacodynamical model will be described hereinafter.

If desired, the results of the first and second type of blood tests of FIG. 1 may also be computer generated. The herein described mathematical model might be used in the context of the present invention which model takes into account biochemical aspects and pharmacodynamical aspects of characteristics of the examined or monitored blood circulation. In other words the method of visualizing a bridge therapy process may also be completely based on simulated values of a first and second type of blood tests. However, if desired, a combination of measured values taken from a blood sample and simulated, calculated or modeled values is comprised in the present invention. Also only measured values may be used to monitor the time progression of the values of the first and second blood tests.

Figure 2:
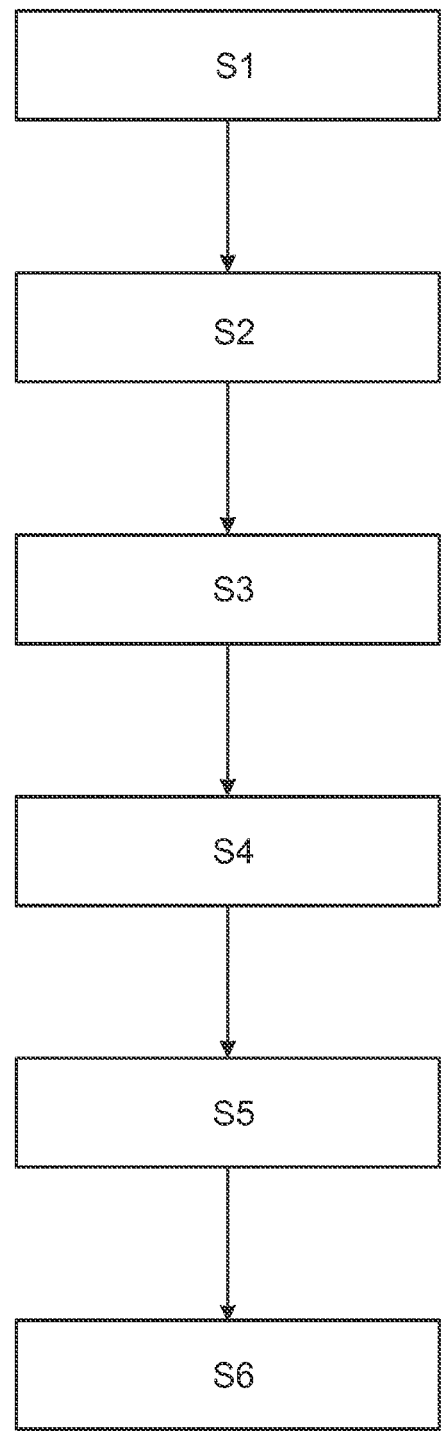

FIG. 2 schematically shows another method of visualizing a bridging therapy process according to another exemplary embodiment of the invention. Regarding the shown steps (S1) to (S4) it is referred to the complete description regarding FIG. 1 which was previously presented. In addition to the steps (S1) through (S4), FIG. 2 shows steps (S5) and (S6). The method of FIG. 2 comprises a displaying of a third measured or simulated value of the first type of blood test, which third measured or simulated value indicates a third effect of a heparin-like drug on the haemostatic situation. This third effect might be similar to the first effect, however it takes place or has taken place at another point in time as the third measured or simulated value is measured or simulated in or for a different point in time compared to the first measured value. Furthermore, the presented method comprises the step of simultaneously displaying a fourth measured or simulated value of a second type of blood test simultaneously to the displaying of the third measured value. The fourth measured value indicates a fourth effect of vitamin K antagonist type anticoagulant on the haemostatic situation and thereby displays a time progression of the haemostatic situation.

In other words, the visualizing method of FIG. 2 displays to the user, two distinct points in an X and Y coordinate system, wherein the X axis may relate to aPTT values and the Y axis to INR values. However, the person skilled in the art directly and unambiguously derives from this exemplary embodiment that also other tests may be used in such an exemplary X and Y coordinate system representation to display the risk of thrombosis and the risk of bleeding in a proper and efficient way to the user. So, time progression of the risk of bleeding and risk of thrombosis is displayable to the user. This might be extended by a computer model allowing for predictions based on for example entering assumptions like changing INR values or a desired change in the dosage regime for used drugs.

Figure 6:
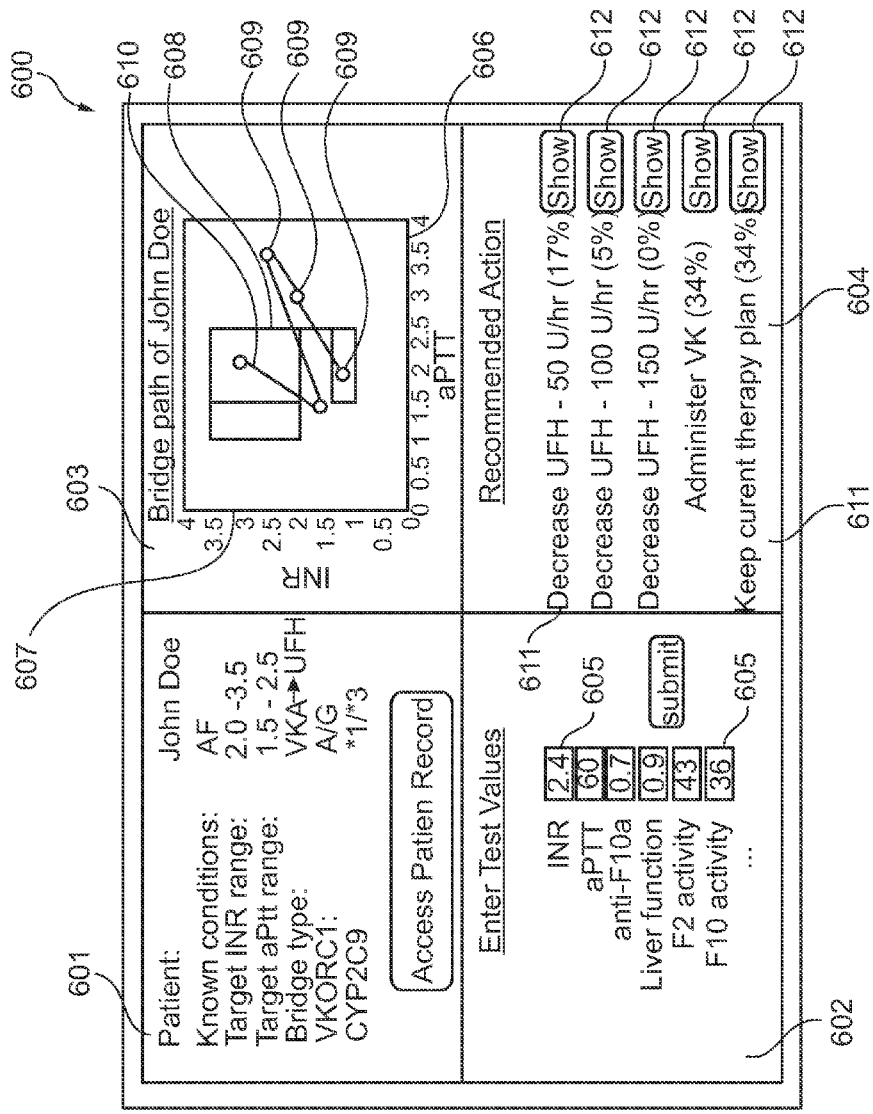
FIG. 6 schematically shows an graphical representation as it can be used during an exemplary embodiment of the present invention.

In other words, FIG. 2 is an abstract representation of what can be seen in FIG. 6, right hand side, in the aPTT and INR coordinate system. Each depicted point in said coordinate system can be interpreted as a first measured value and a second measured value with regard to the first type of blood test being aPTT and with regard to a second type of blood test being INR.

Figure 3:
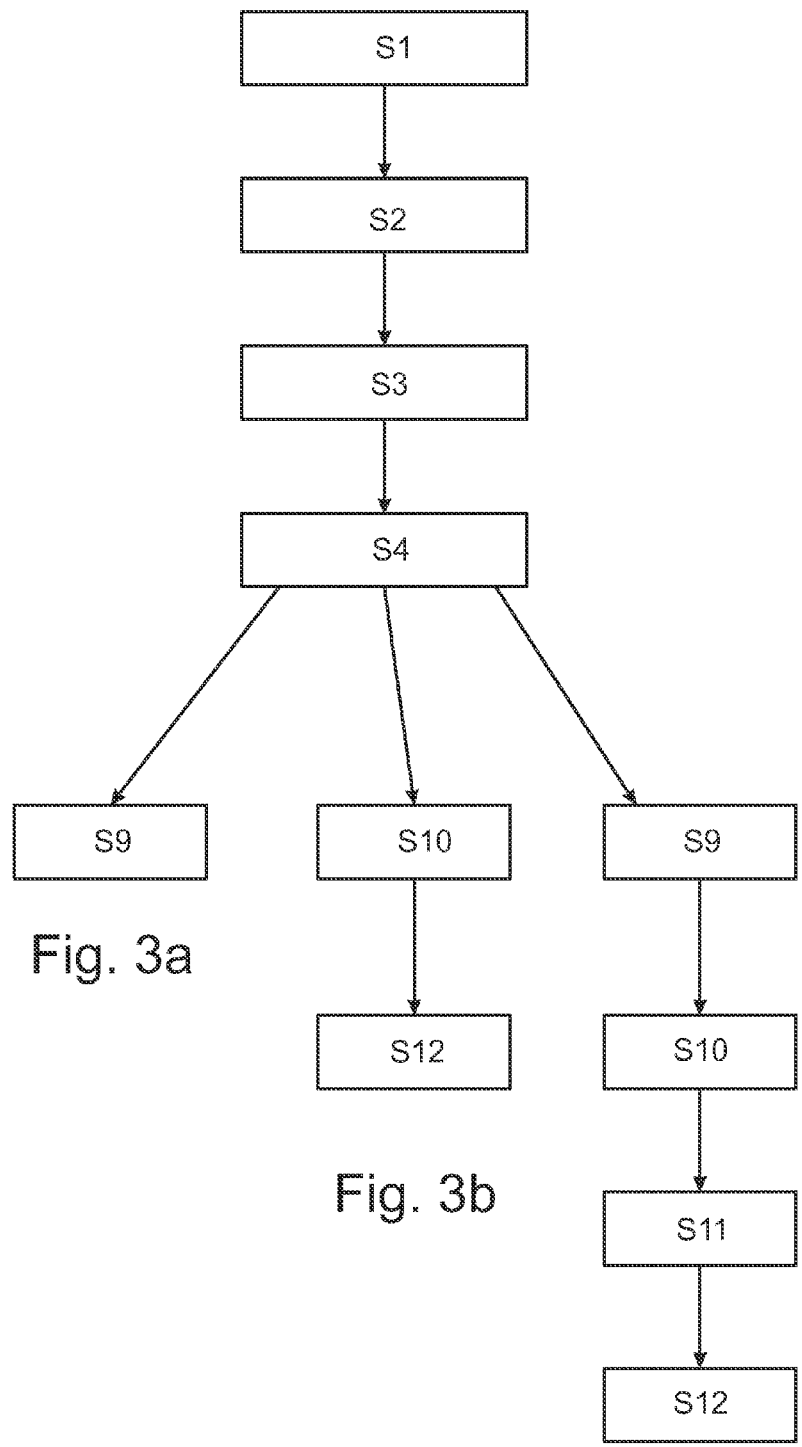

FIGS. 3a to 3c respectively describe an exemplary method as an embodiment of the present invention. FIG. 3a shows a method of visualizing a bridge therapy process in which (S1) to (S4) are the steps that have been described with regard to FIG. 1. After step (S4) has been performed by the method of FIG. 3a, the method becomes a computer support decision method as step (S9) is performed. Step (S9) describes calculating a prediction of the haemostatic situation of the blood circulation by combining a biochemical model of the blood circulation and a pharmacodynamical model of the blood circulation.

In the exemplary embodiment of FIG. 3b an effect of an anticoagulant drug during a predetermined time is calculated by using the above described pharmacodynamical model in step (S10). The calculation results in a calculated pharmacodynamical effect. If desired, such an effect may be used later in other exemplary embodiments of the invention. In other words, the exemplary embodiment of FIG. 3b comprises a mathematical model which only takes into account the pharmacodynamical model in order to assist the bridging process. In other words the hemostatic risk is based directly on the modeled drug concentration in the blood or the resulting changes in active coagulation proteins.

If desired, also only the biochemical model might be used in a calculation step for predicting the haemostatic situation. However, such an embodiment in which only the biochemical model is used is not shown.

The exemplary embodiment of FIG. 3c shows a use of a mathematical model which takes into account a pharmacodynamical model in step (S10), in order to base the prediction on absorption, distribution, metabolism, and excretion properties of the patient's response to the drugs. The examined blood circulation system may comprise several vessels. Furthermore, the distribution dynamics and/or distribution kinetics of a drug in said vessel system is considered as the pharmacodynamical model might have been generated based on these aspects.

The pharmacodynamical model may be based not only on distribution in the vessels but in the whole body. So it starts with absorbing the drug, than distribution of the drug occurs throughout the body also leading to a certain amount of drug in the blood circulation, and so on. The amount of drug in the blood may be a parameter important to the presented model.

Furthermore, a biochemical model is used for calculating the prediction of the haemostatic situation in step (S11). The biochemical model calculates a coagulation effect and/or a fibrin polymerization effect based on the calculated pharmacodynamical effect in step (S11). If desired a prediction value of the haemostatic situation may be displayed to a user in step (S12). Therein, the prediction value is based on at least one of the calculated pharmacodynamical effects, the calculated coagulation effect and the calculated fibrin polymerization effect. In a complete version all three effects are used as basis for the prediction. As can bee seen from the comprised Tables 1 to 5, the coagulation cascade is considered (Table 1), fibrin polymerization is considered (Table 2), effects of unfractionated heparin (UFH) and low-molecular weight heparin (LMWH) or other heparin-like drugs (Table 3) are considered by means of the mathematical model. Furthermore, in Tables 4 and 5 ordinary differential equations that might be incorporated partially or also completely in the mathematical model regarding pharmacodynamical effects of unfractionated heparin (UFH) and LMWH. Furthermore, Table 5 shows ordinary differential equations which might be incorporated in the mathematical model if desired. The equations regard pharmacokinetic and pharmacodynamical effects of Warfarin, which is a vitamin K antagonist (VKA).

In other words the mathematical model can, if desired, comprise partially or completely the reaction mechanisms that are disclosed in Tables 1 to 3. Also the ordinary differential equations disclosed in Tables 4 and 5 may be integrated into the mathematical model according to the user's desire. In other words, also a combination between different reaction mechanisms out of Tables 1 to 3 with ordinary differential equations out of Tables 4 and 5 are possible. In other words the person skilled in the art may take from the presented tables 1 to 5 the features he is interested in regarding his special medical case. Thus, it is made clear that the model presented herein is just a version of the model, and that this model can be adapted, extended, reduced or even completely replaced by another mathematical model which takes into account biochemical and pharmacodynamical aspects.

The gist of this mathematical model can be seen in the combination of a biochemical model calculating coagulation cascade and fibrin polymerization. Thus, "enzymatic conversion" in combination with "complex assembly" can be taken into account during the prediction.

The mathematical model used in the context of the present invention will be explained in more detail hereinafter. This model may be implemented in every herein described embodiment of the invention. It is of utmost importance that the below presented model is just one exemplary embodiment of the mathematical model according to the present invention.

Mathematical Definition of the Model

The mathematical model can be considered to consist of three separate modules: coagulation cascade, fibrin polymerization and pharmacokinetics and pharmacodynamics (PK/PD) of anticoagulant drugs. Whereas the first two modules are based on the underlying (protein) interactions of the coagulation response and are used to simulate in vitro tests like the thrombin generation assay, prothrombin time (PT) and activated partial thromboplastin time (aPTT), the latter is based on compartment modeling which is used to simulate the (long-term) kinetics and effect of the anticoagulants such as unfractionated heparin (UFH), low-molecular weight heparin (LMWH) and warfarin in the human body. The way this is coupled is as follows: the effect of the anticoagulants is simulated for the whole bridging period, at predefined time points a 'snapshot' is taken of the disturbed situation in the blood (symbolizing a blood sample taken from the patient) and used as input to the biochemical model of the coagulation cascade and fibrin polymerization.

Biochemical Model

The physiological system of biochemical reactions may be represented as a closed volume element, representing a certain volume of blood plasma in in vitro tests. Hence, there is no transport in or out of this volume and clearance of proteins is assumed to be not significant on this time-scale (minutes). This means that there is conservation of mass in the volume element. Besides that it is assumed that diffusion in the mixture does not significantly influence the reaction velocities.

The mathematical model of the coagulation cascade and fibrin polymerization consists of 216 state variables (concentrations of proteins and protein complexes) and 100+ reaction rate constants that are used to parameterize 91 reactions. An overview of the reactions is given in Table 1, Table 2 and Table 3. All states, initial concentrations and kinetic parameters were defined as non-negative real numbers, IR+0. The initial concentrations of the proteins are inferred from values reported in literature or set to the actual measured concentrations. The model's kinetic parameters were estimated from in-house generated experimental data by means of solving the inverse problem. Nevertheless, the kinetic parameters (but also the initial concentrations) are subjected to a continuous update process to improve the accuracy of the found values by means of additional experiments and analyses. The functional description of the state equations can be represented as follows (in state space formulation).

$$\frac{dx}{dt} = f(x(t), u(t), \theta), \text{ with } x_0 = x(t_0) \tag{1}$$

Where x is the state vector, u the input vector of the test conditions (e.g. certain tissue factor concentration to simulate the PT), x0 is the vector of initial concentrations and f is a vector field with non-linear functions parameterized with $\theta$. The output, y, of the state model can be characterized by:

$$y(t,\theta) = \underline{C} x(t,\theta) \tag{2}$$

Where matrix C selects a number of 'interesting' states of the model output. The 91 reaction mechanisms derived from literature were classified as either one of two types of elementary reaction mechanisms. These reaction mechanisms were complex assembly and enzymatic conversion. Complex assembly is the process where substrate A and B react to form complex A-B. It features in the formation of coagulation complexes (e.g. FXa-FVa, FIXa-FVIIIa) and inhibition of activated proteins by stochiometric inhibitors (e.g. FIIa-AT-III, TF-FVIIa-FXa-TFPI). The related reaction equation reads:

$$A + B \underset{k_{-1}}{\overset{k_1}{\rightleftarrows}} A - B \tag{3}$$

The association rate constant of complex formation, k1, is a second order rate constant and the dissociation rate constant of A and B from A-B, k−1, is a first-order rate constant. In some cases the association reaction is irreversible, which means the complex is stable and will not dissociate, e.g. inhibition of FIIa by AT-III. Reaction scheme (3) was converted to the following set of ordinary differential equations (ODEs) describing the change in concentration, represented by [ . . . ], in time:

$$\frac{\partial [A]}{\partial t} = \frac{\partial [B]}{\partial t} = -\frac{\partial [A-B]}{\partial t} = -k_1[A][B] + k_{-1}[A-B] \tag{4}$$

The enzymatic conversion of proteins by enzymes was the second type of reaction mechanism exploited in the coagulation model. All activation processes in the hemostasis model correspond to this type of reaction. The reaction scheme of enzymatic conversion can be represented schematically as:

(5)

Where E is the enzyme and S the substrate concentration that is converted into product P by E. Enzymatic conversion of proteins was implemented in the mathematical model as follows:

$$\frac{\partial [E]}{\partial t} = -k_1[E][S] + k_{-1}[E-S] + k_2[E-S] \qquad (6)$$

$$\frac{\partial [S]}{\partial t} = -k_1[E][S] + k_{-1}[E-S] \qquad (7)$$

$$\frac{\partial [E-S]}{\partial t} = k_1[E][S] - k_{-1}[E-S] - k_2[E-S] \qquad (8)$$

$$\frac{\partial [P]}{\partial t} = k_2[E-S] \qquad (9)$$

Most of the proteins or protein-complexes participate in multiple reactions in the biochemical model, hence all reactions that the protein or protein-complex is participating in have to be accounted for in the ODE of that specific protein's or protein-complex' concentration. This results in one ODE per protein or protein-complex, which consists of a summation of ODE contributions from all reactions that the protein is participating in. This is represented mathematically as follows (an alternative representation of equation (1)).

$$\frac{\partial x}{\partial t} = \underline{SR}(x) = \sum_{i=1}^{m} S^i R_i(x) \qquad (10)$$

Where x is the vector of concentrations of the different substrates, S is the matrix with reaction rate constants and R is the reaction matrix. Each column of the stochiometric matrix Si corresponds to a particular reaction.

PK/PD Model

The mathematical model that simulates the long-term kinetics and effects of the anticoagulants is based on a combination of compartment models that are generally used in PK/PD modeling. Since the PK/PD equations are not as standardized as the biochemical equations (only complex assembly and enzymatic catalysis), the complete ODEs of each state are shown in Table 4 and Table 5. The ODEs belonging to the pharmacokinetic properties of unfractionated heparin and low-molecular weight heparin are shown in Table 4. As a result of these ODEs the blood kinetics of both types of heparin can be calculated. The effects of both heparins are on the activity of AT-III, and this is represented by equations v78 v91 in the biochemical model, which uses the blood concentrations of UFH and LMWH at the moment of blood withdrawal as input. The ODEs corresponding to the blood kinetics of warfarin and its effect on the production of several coagulation proteins by inhibiting the vitamin K cycle are given in Table 5. The blood concentrations of the coagulation proteins at the moment of blood withdrawal are used as input for the biochemical model.

The Tables 1 to 5 are shown in the following. The mathematical model described herein may thus take into account several or all reaction mechanisms v1 to v91. The person skilled in the art will combine them as needed or desired. Additionally the ordinary differential equations described under PKPD1 to PKPD17 may partially or completely be implemented in the mathematical model.

The used model may also be described as follows: The computer model may be seen as a representation of the coagulation cascade and fibrin polymerization as a set of reaction mechanisms. The time dynamics of each reaction mechanism may be described as an ordinary differential equation or ODE that involves the concentration(s) of the protein(s) and/or chemical molecule(s) that are involved in the reaction and the reaction rate parameter(s). By summation of all reaction mechanisms in which a particular protein or other kind of chemical molecular is involved (a protein or molecule can participate in more than one reaction), the time dynamics of the concentration of that particular protein or other kind of chemical entity may be calculated. Doing this for all proteins or molecules, the whole system can calculate and keep track of the evolution of all proteins and molecules over time, however for this one may require, beside the reaction topology, also the numerical values of the model parameters. These model parameters include the initial conditions of the system, i.e. the concentration of all proteins and molecules at t=0 (e.g. before onset of bridging therapy), and the reaction rate parameters of the reaction mechanisms. Part of the initial concentrations that are the most important to the outcome of the system are measured from the patient (in the laboratory or clinic), whereas others, less determining proteins, are taken from literature (average patient values, possibly corrected for gender and age, etc.). The reaction rate parameters may be derived via solving an inverse problem, i.e. model fitting to experimental data. The system of coupled ODEs may be solved numerically, using the numerical values of the model parameters, by employing standard ODE integration algorithms.

The expected future evolution of the aPTT and INR, as predicted by the computer model, are shown on the user interface together with the evolution of the measured aPTT and INR during the bridging period, which are/were entered in the user interface by the user. These aPTT- and INR-predictions are calculated by the computer model based on the initial concentrations that are determined in the tests, prederived reaction rate parameters and population average values for the unknown concentrations. Previously measured aPTT and INR values in combination with other (clinical) measurements, such as the activity of the vitamin K-dependent proteins, liver function, are used to optimize the predictions to be more patient specific, i.e. personalized therapy planning.

The progression of the measured and predicted aPTT and INR during the bridging period is referred to as bridging path (see representation in the upper right corner of the user interface example of FIG. 6). The user can use the combined measured and predicted bridging path to assess the patient's risk and make appropriate adaptations to the therapy plan. The different therapy options can be simulated by the computer model and the predicted effects thereof are visualized on the user interface.

An improvement of the said model would be to link the application directly to the hospital IT system. In this way the laboratory measurements, patient records and decided therapy plan can be directly communicated to the appropriate other applications of the hospital IT system, or vice versa. Another embodiment could be to replace the aPTT and/or INR tests by other tests that are better estimates of the effect of heparin and VKA treatment. For example, the anti-Factor 10a assay is generally used to monitor the effects of LMWH. In case the patient is treated with LMWH this would suggest to use the output of the anti-factor 10a assay on the x-axis instead of the aPTT to monitor the effect of LMWH. In addition, in the future new and better tests reflecting the hemostatic balance might be invented. Such test may also be used in combination with the present invention.

TABLE 1

All reaction mechanisms incorporated in the computer model of the coagulation cascade. It should be noted that in this table the official gene symbols are used instead of the popular scientific names

| Reaction | Name | Type | Substrates | Products | Cofactors/Catalyst | Reaction site |
|---|---|---|---|---|---|---|
| v1 | F3-F7a complex assembly | Complex assembly | F3, F7a | F3-F7a | | Endothelial membrane |
| v2 | F3-F7 complex assembly | Complex assembly | F3, F7 | F3-F7 | | Endothelial membrane |
| v3 | F7 activation (1) | Catalysis | F7 | F7a | F3-F7a | Endothelial membrane |
| v4 | F7 activation (2) | Catalysis | F7 | F7a | F10a | Endothelial membrane |
| v5 | F7 activation (3) | Catalysis | F7 | F7a | F9a | Endothelial membrane |
| v6 | F7 activation (4) | Catalysis | F7 | F7a | F2a | |
| v7 | F9 activation (1) | Catalysis | F9 | F9a | F11a, negative phospholipids | |
| v8 | F9 activation (2) | Catalysis | F9 | F9a | F3-F7a | Endothelial membrane |
| v9 | F9a degradation | Degradation | F9a | | | Blood plasma |
| v10 | F8 activation (1) | Catalysis | F8 | F8a | F2a | Blood plasma?? |
| v11 | F8 degradation | Degradation | F8a | | PROCa-PROS1-F5ac | Platelet membrane |
| v12 | F9a-F8a complex assembly | Complex assembly | F9a, F8a | F9a-F8a | Ca2+, neg phospholipid | Platelet membrane |
| v13 | F2 activation (1) | Catalysis | F2 | F2a | F10a | Blood plasma |
| v14 | F2 activation (2) | Catalysis | F2 | F2a | F10a-F5a | Platelet membrane |
| v15 | F2a degradation | Degradation | F2a | | | Blood plasma |
| v16 | F5 activation | Catalysis | F5 | F5a | F2a | Blood plasma |
| v17 | F5 anticoagulant formation | Catalysis | F5 | F5ac | PROCa | Blood plasma |
| v18 | F5a degradation | Degradation | F5a | | PROCa-PROS1 | Blood plasma/endothelial membrane |
| v19 | F10 activation (1) | Catalysis | F10 | F10a | F3-F7a | Endothelial membrane |
| v20 | F10 actication (2) | Catalysis | F10 | F10a | F9a-F8a | Platelet membrane |
| v21 | F10 activation (3) | Catalysis | F10 | F10a | F9a | Blood plasma?? |
| v22 | F10a degradation | Degradation | F10a | | | Blood plasma |
| v23 | F10a-F5a complex assembly | Complex assembly | F10a, F5a | F10a-F5a | Ca2+, neg phospholipid | Platelet membrane |
| v24 | PROC activation (1) | Catalysis | PROC | PROCa | F2a | Blood plasma |
| v25 | PROS1-C4BP complex assembly | Complex assembly | PROS1, C4BP | PROS1-C4BP | | Blood plasma |
| v26 | PROCa-PROS1 complex assembly | Complex assembly | PROCa, PROS1 | PROCa-PROS1 | Ca2+, neg phospholipid | Platelet membrane |
| v27 | PROCa-PROS1-F5ac complex assembly | Complex assembly | PROCa-PROS1, F5ac | PROCa-PROS1-F5ac | Ca2+, neg phospholipid | Platelet membrane |
| v28 | F13 activation | Catalysis | F13 | F13a | F2a,Ca2+ (at least 1 mM) | Blood plasma |
| v29 | F12 activation (1) | Catalysis | F12 | F12a | F12a, negative phospholipds | Negative surface |
| v30 | F12 activation (2) | Catalysis | F12 | F12a | KLKB1a | Blood plasma |
| v31 | F11 activation (3) | Catalysis | F12 | F12a | KNG1 | Blood plasma |
| v32 | F12a degradation | Degradation | F12a | | | Blood plasma?? |
| v33 | KLKB1 activation | Catalysis | KLKB1 | KLKB1a | F12a | Blood plasma |
| v34 | F11 activation (1) | Catalysis | F11 | F11a | F12a | Blood plasma |
| v35 | F11 activation (2) | Catalysis | F11 | F11a | F2a, negative phospholipids | Negative surface |
| v36 | F11 activation (3) | Catalysis | F11 | F11a | F11a, negative phospholipids | Negative surface |
| v37 | F11a degradation | Degradation | F11a | | | Blood plasma |
| v38 | CPB2 activation (1) | Catalysis | CPB2 | CPB2a | F2a | Blood plasma |
| v39 | CPB2a degradation | Degradation | CPB2a | | | Blood plasma |
| v40 | F10a-TFPI complex assembly | Complex assembly | TFPI, F10a | F10a-TFPI | | Blood plasma?? |
| v41 | F10a-F3-F7a-TFPI complex assembly | Complex assembly | F10a-TFPI, F3-F7a | F10a-F3-F7a-TFPI | Ca2+ | Endothelial membrane |

TABLE 1-continued

All reaction mechanisms incorporated in the computer model of the coagulation cascade. It should be noted that in this table the official gene symbole are used instead of the popular scientific names

| Reaction | Name | Type | Substrates | Products | Cofactors/ Catalyst | Reaction site |
|---|---|---|---|---|---|---|
| v42 | F3-F7a-TFPI complex assembly | Complex assembly | F3-F7a, TFPI | F3-F7a-TFPI | | Endothelial membrane |
| v43 | F11a-SERPINC1 complex assembly | Complex assembly | F11a, SERPINC1 | F11a-SERPINC1 | SERPIND1 | Blood plasma |
| v44 | F12a-SERPINC1 complex assembly | Complex assembly | F12a, SERPINC1 | F12a SERPINC1 | SERPIND1 | Blood plasma |
| v45 | F9a-SERPINC1 complex assembly | Complex assembly | F9a, SERPINC1 | F9a-SERPINC1 | SERPIND1 | Blood plasma |
| v46 | F2a-SERPINC1 complex assembly | Complex assembly | F2a, SERPINC1 | F2a-SERPINC1 | SERPIND1 | Blood plasma |
| v47 | F10a-SERPINC1 complex assembly | Complex assembly | F10a, SERPINC1 | F10a-SERPINC1 | SERPIND1 | Blood plasma |
| v48 | F3-F7a-SERPINC1 complex assembly | Complex assembly | F3-F7a, SERPINC1 | F3-F7a-SERPINC1 | SERPIND1 | Blood plasma |
| v49 | PROCa-SERPINA1 complex assembly | Complex assembly | PROCa, SERPINA1 | PROCa-SERPINA1 | | Blood plasma |
| v50 | PROCa-SERPINA5 complex assembly | Complex assembly | PHOCa, SERPINA5 | PROCa-SERPINA5 | Heparin dependent | Blood plasma |
| v51 | F2a-SERPINA5 complex assembly | Complex assembly | F2a, SERPINA5 | F2a-SERPINA5 | Heparin dependent | Blood plasma |
| v52 | F10a-SERPINA5 complex assembly | Complex assembly | F10a, SERPINA5 | F10a-SERPINA5 | Heparin dependent | Blood plasma |
| v53 | KLKB1a-SERPINA5 complex assembly | Complex assembly | KLKB1a, SERPINA5 | KLKB1a-SERPINA5 | | Blood plasma?? |
| v54 | PROZ-SERPINA10 complex assembly | Complex assembly | PHOZ, SERPINA10 | PROZ-SERPINA10 | | Blood plasma |
| v55 | F9a-SERPINA10 complex assembly | Complex assembly | F9a, SERPINA10 | F9a-SERPINA10 | | Blood plasma |
| v56 | F10a-PROZ-SERPINA10 complex assembly | Complex assembly | PROZ-SERPINA10, F10a | F10a-PROZ-SERPINA10 | Ca2+, Phospholipids | Membrane |
| v57 | F11a-SERPINA10 complex assembly | Complex assembly | F11a, SERPINA10 | F11a-SERPINA10 | | Blood plasma |
| v58 | PROCa-SERPINE1 complex assembly | Complex assembly | PROCa, SERPINE1 | PROCa-SERPINE1 | | Blood plasma?? |
| v59 | F2a-SERPINE1 complex assembly | Complex assembly | F2a, SERPINE1 | F2a-SERPINE1 | | Blood plasma |
| v60 | VTN-SERPINE1 complex assembly | Complex assembly | VTN, SERPINE1 | VTN-SERPINE1 | | Membrane surface |
| v61 | F2a-VTN-SERPINE1 complex assembly | Complex assembly | F2a, VTN-SERPINE1 | F2a-VTN-SERPINE1 | | Membrane surface |
| v62 | CPB2a-SERPINE1 complex assembly | Complex assembly | CPB2a, SERPME1 | CPB2a-SERPINE1 | | Blood plasma |
| v63 | SERPINE1 degradation | Degradation | SERPINE1 | | | Blood plasma?? |
| v64 | F11a-SERPINE1 complex assembly | Complex assembly | F11a, SERPING1 | F11a-SERPING1 | | Blood plasma?? |
| v65 | F12a-SERPING1 complex assembly | Complex assembly | F12a, SERPING1 | F12a-SERPING1 | | Blood plasma?? |
| v66 | KLKB1-SERPING1 complex assembly | Complex assembly | KLKB1a, SERPING1 | KLKB1a-SERPING1 | | Blood plasma?? |
| v67 | F2a-α2-M complex assembly | Complex assembly | F2a, α2-M | F2a-α2-M | | |
| v68 | Substrate catalysis | Catalysis | subs | subsa | F2a | |
| v69 | Substrate catalysis | Catalysis | subs | subsa | F2a-α2-M | |

TABLE 2

All reaction mechanisms incorporated in the computer model of the fibrin polymerization.

| Reaction | Name | Type | Substrates | Products | Cofactors/ Catalyst | Reaction site |
|---|---|---|---|---|---|---|
| v70 | FpA cleavage from Fg | Catalysis | Fg | desAA-Fg, 2 FpA | F2a | Blood plasma |
| v71 | FpB cleavage from Fg | Catalysis | Fg | desBB-Fg, 2 FpB | F2a | Blood plasma |
| v72 | FpA cleavage from desAA-Fg | Catalysis | desAA-Fg | Fn, 2 FpA | F2a | Blood plasma |
| v73 | FpB cleavage from desBB-Fg | Catalysis | desBB-Fg | Fn, 2 FpB | F2a | Blood plasma |
| v74 | FpA cleavage from Fg-F2a | Catalysis | Fg-F2a | desAA-Fg-F2a | F2a | Blood plasma |
| v75 | FpB cleavage from Fg-F2a | Catalysis | Fg-F2a | desBB-Fg-F2a | F2a | Blood plasma |

TABLE 2-continued

All reaction mechanisms incorporated in the computer model of the fibrin polymerization.

| Reaction | Name | Type | Substrates | Products | Cofactors/Catalyst | Reaction site |
|---|---|---|---|---|---|---|
| v76 | Protofibril formation/growth | Complex assembly* | $P_n, P_m$ | $P_{n+m}$ | | Blood plasma |
| v77 | Fiber formation/growth | Complex assembly** | $F_o, F_p$ | $F_{n+m}$ | Fn | Blood plasma |

*$P_n + P_m \rightarrow P_{n+m} \forall n + m \geq 29, n > 0, m > 0$

**$F_o + F_p \rightarrow P_{n+m} \forall o + p \geq 9, o > 0, p > 0$

TABLE 3

All reaction mechanisms incorporated in the computer model regarding the effect of unfractionated heparin (UFH) and low-molecular weight heparin (LMWH) on the function of AT-III. It should be noted that in this table the official gene symbol of AT-III (SERPINC1) is used instead of the popular scientific names.

| Reaction | Name | Type | Substrates | Products | Cofactors/Catalyst | Reaction site |
|---|---|---|---|---|---|---|
| v78 | SERPINC1-UFH complex assembly | Complex assembly | SERPINC1, UFH | SERPINC1-UFH | | Blood plasma |
| v79 | F11a-SERPINC1-UFH complex assembly | Complex assembly | F11a, SERPINC1-UFH | F11a-SERPINC1-UFH | | Blood plasma |
| v80 | F9a-SERPINC1-UFH complex assembly | Complex assembly | F9a, SERPINC1-UFH | F9a-SERPINC1-UFH | | Blood plasma |
| v81 | F2a-SERPINC1-UFH complex assembly | Complex assembly | F2a, SERPINC1-UFH | F2a-SERPINC1-UFH | | Blood plasma |
| v82 | F10a-SERPINC1-UFH complex assembly | Complex assembly | F10a, SERPINC1-UFH | F10a-SERPINC1-UFH | | Blood plasma |
| v83 | F3-F7a-SERPINC1-UFH complex assembly | Complex assembly | F3-F7a, SERPINC1-UFH | F3-F7a-SERPINC1-UFH | | Blood plasma |
| v84 | F10a-F5a-SERPINC1-UFH complex assembly | Complex assembly | F10a-F5a, SERPINC1-UFH | F10a-F5a-SERPINC1-UFH | | Blood plasma |
| v85 | SIRPINC1-LMWH complex assembly | Complex assembly | SERPINC1, LMWH | SERPINC1-LMWH | | Blood plasma |
| v86 | F11a-SERPINC1- LMWH complex assembly | Complex assembly | F11a, SERPINC1-LMWH | F11a-SERPINC1-LMWH | | Blood plasma |
| v87 | F9a-SERPINC1-LMWH complex assembly | Complex assembly | F9a, SERPINC1-LMWH | F9a-SERPINC1-LMWH | | Blood plasma |
| v88 | F2a-SERPINC1-LMWH complex assembly | Complex assembly | F2a, SERPINC1-LMWH | F2a-SERPINC1-LMWH | | Blood plasma |
| v89 | F10a-SERPINC1-LMWH complex assembly | Complex assembly | F10a, SERPINC1-LMWH | F10a-SERPINC1-LMWH | | Blood plasma |
| v90 | F3-F7a-SERPINC1-LMWH complex assembly | Complex assembly | F3-F7a, SERPINC1-LMWH | F3-F7a-SERPINC1-LMWH | | Blood plasma |
| v91 | F10a-F5a-SERPINC1-LMWH complex assembly | Complex assembly | F10a-F5a, SERPINC1-LMWH | F10a-F5a-SERPINC1-LMWH | | Blood plasma |

TABLE 4

The ordinary differential equations incorporated in the computer model regarding the PK effort of unfractionated heparin (UFH) and low-molecular weight heparin (LMWH). All states are described in more detail in the last column, all other entitles in the equations (e.g. IV, keUFH, kaLMWH) are model constants.

| Reaction | Name | Equation | Description |
|---|---|---|---|
| PKPD1 | UFH in blood compartment | $\dfrac{d[UFH]}{dt} = \dfrac{IV}{Vd_{UFH}} - k_{eUFH}[UFH]$ | [UFH]: concentration of UFH in blood compartment |
| PKPD2 | LMWH in absorption compartment | $\dfrac{dA_{LMWH}}{dt} = -k_a A_{LMWH}$ | $A_{LMWH}$: amount of LMWH in absorption compartment |
| PKPD3 | LMWH in blood compartment | $\dfrac{d[LMWH]}{dt} = k_a \dfrac{A_{LMWH}}{Vc_{LMWH}} - k_{12,LMWH}[LMWH] + k_{21,LMWH}\dfrac{A_{LMWH,p}}{Vc_{LMWH}} - k_{eLMWH}[LMWH]$ | [LMWH]: concentration of LMWH in blood compartment |

TABLE 4-continued

The ordinary differential equations incorporated in the computer model regarding the PK effort of unfractionated heparin (UFH)
and low-molecular weight heparin (LMWH). All states are described in more detail in the last column,
all other entitles in the equations (e.g. IV, keUFH, kaLMWH) are model constants.

| Reaction | Name | Equation | Description |
| --- | --- | --- | --- |
| PKPD4 | LMWH in peripheral compartment | $\dfrac{dA_{LMWH,p}}{dt} = k_{12,LMWH}[LMWH]Vc_{LMWH} - k_{21,LMWH}A_{LMWH,p}$ | $A_{LMHH,p}$: amount of LMWH in peripheral compartment |

TABLE 5

The ordinary differential equations incorporated in the computer model regarding the PK/PD effect of warfarin.
All states described in more detail in the last column, all other entitles in the equations
(e.g. $k_a$, $k_e$, $V_d$, $VK_{prod}$) are model constants.

| Reaction | Name | Equation | Description |
| --- | --- | --- | --- |
| PKPD5 | Warfarin absorption | $\dfrac{dA_{warf}}{dt} = -k_a\, A_{warf}$ | $A_{warf}$: amount of warfarin in the absorption compartment |
| PKPD6 | Warfarin in blood compartment | $\dfrac{d[warf]}{dt} = k_a \dfrac{A_{warf}}{V_d} - k_e[warf]$ | [warf]: concentration of warfarin |
| PKPD7 | Vitamin K in peripheral compartment | $\dfrac{dA_{VK,p}}{dt} = k_{12}[VK]VcK - k_{21}A_{VK,p}$ | $A_{VK,p}$: amount of vitamin K in peripheral compartment |
| PKPD8 | Vitamin K in blood compartment | $\dfrac{d[VK]}{dt} = VK_{prod} - dvk2[VK]\left(1 - \dfrac{I_{max}[warf]}{IC_{50}+[warf]}\right) - dvk[VK] + dvko[VKO]\left(1 - \dfrac{I_{max}[warf]}{IC_{50}+[warf]}\right) - k_{12}[VK] + k_{21}\dfrac{A_{VK,p}}{VcK}$ | [VK]: concentration of vitamin K in blood compartment |
| PKPD9 | Vitamin KH$_2$ in blood compartment | $\dfrac{d[VKH_2]}{dt} = dvk2[VK]\left(1 - \dfrac{I_{max}[warf]}{IC_{50}+[warf]}\right) - dvkh2[VKH_2]$ | [VKH$_2$]: concentration of KH$_2$ in blood compartment |
| PKPD10 | Vitamin KO in blood compartment | $\dfrac{d[VKH_2]}{dt} = dvk2[VK]\left(1 - \dfrac{I_{max}[warf]}{IC_{50}+[warf]}\right) - dvkh2[VKH_2]$ | [VKH$_2$]: concentration of KO in blood compartment |
| PKPD11 | F2 in blood compartment | $\dfrac{d[F2]}{dt} = pF2 - dF2[F2]$ | [F2]: concentration of F2 in blood compartment |
| PKPD12 | F7 in blood compartment | $\dfrac{d[F7]}{dt} = pF7 - dF7[F7]$ | [F7]: concentration of F2 in blood compartment |
| PKPD13 | F8 in blood compartment | $\dfrac{d[F9]}{dt} = pF9 - dF9[F9]$ | [F9]: concentration of F2 in blood compartment |

Figure 4:
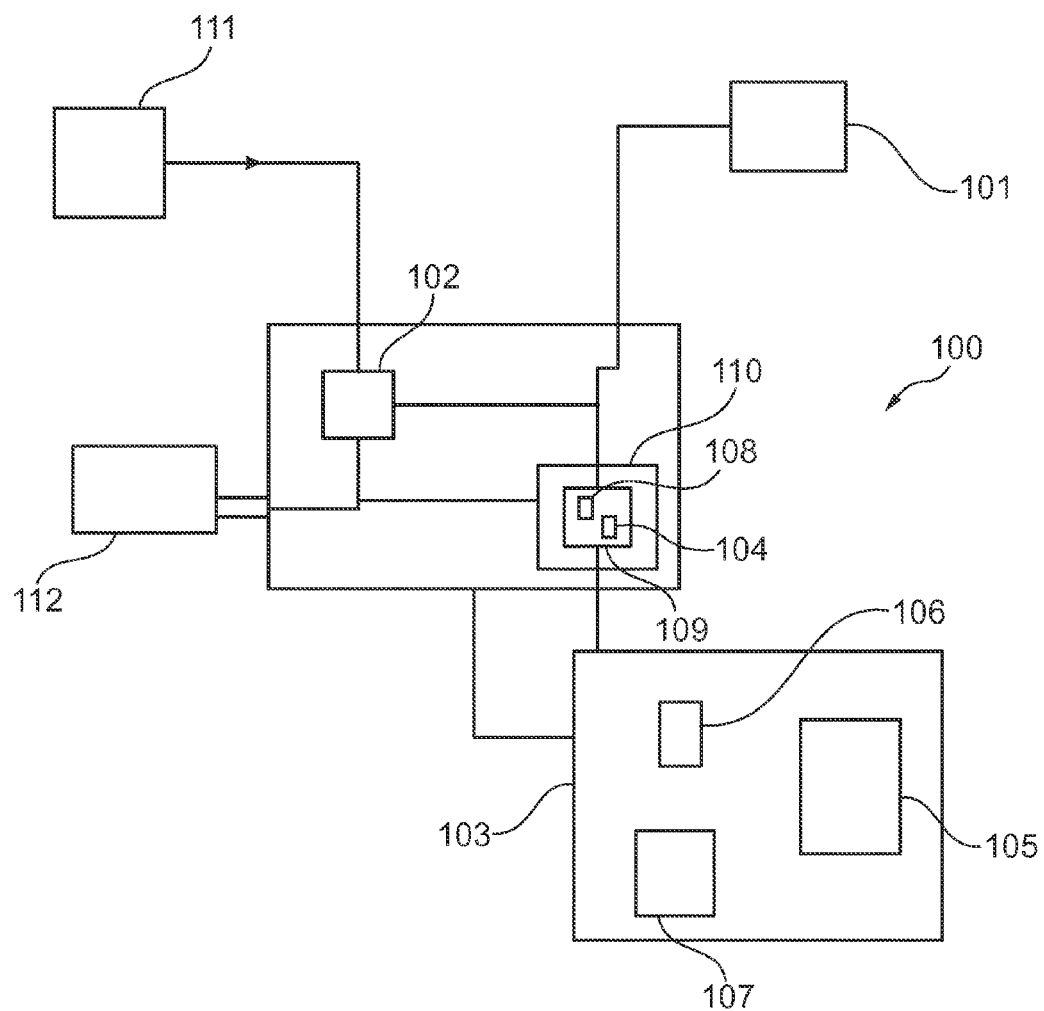
FIG. 4 schematically shows a user interface according to an exemplary embodiment of the invention.

FIG. 4 schematically shows a user interface (100) for visualizing a bridge therapy process. The user interface comprises a receiving arrangement (102) which is configured to receive coagulation data (111). Coagulation data describe a haemostatic situation of the examined blood circulation of a patient. Furthermore, the user interface (100) is configured to display the haemostatic situation of said blood or said blood circulation, for example by a displaying device (103). Furthermore, the user interface is configured to display a first measured value of a first type of blood test, which first measured value indicates a first effect of a heparin-like drug on the haemostatic situation. In addition the user interface is configured to simultaneously display a second measured value of a second type of blood test, which second measured value indicates a second effect of a vitamin K type antagonist type anticoagulant on the haemostatic situation.

The graphical representation which is used to depict said first measured value and said second measured value is exemplarily shown by element (105). It may be seen as responding to the X and Y coordinate system shown in FIG. 6 on the upper right hand side. Furthermore, the displaying device (103) comprises an area (106) in which constant personalized or individual data regarding the patient or the haemostatic function are displayed or can also be entered by a user. In the second zone (107), individual patient data may be displayed and may also be entered by a user. This may for example be an INR value or may also be an amount of anti-coagulant drug which is desired by the user to be checked by the mathematical model that can be performed by the user interface (100). Furthermore, a calculation arrangement (110) is shown wherein the calculation arrangement is configured to calculate a prediction of a haemostatic situation of the blood circulation by combining a biochemical model of the blood circulation and a pharmacodynamical model of the blood circulation.

As the user interface and also the previously presented methods are not applied directly at the patient, no blood circulation or patient is shown in FIG. 4.

The calculation arrangement (110) comprises a program element (104) for visualizing a bridge therapy process, the program element itself may furthermore comprise a biochemical model (108) and a pharmacokinetic or pharmacodynamical model (109) as has been described above and will be described later. Furthermore, a computer-readable medium (112) is shown which is communicating with the receiving section (102) in order to transmit for example coagulation data stored on the storage device or also transmit a program element which was stored on the computer-readable medium.

Furthermore, user interface (100) comprises an entering device (101) in which the user might enter values or also amended administration plan to check how such an amendment would amend the time-resolved progression of the risk of bleeding or risk of thrombosis of the examined blood circulation.

Therein the calculation arrangement (110) is adapted to perform the calculation steps that have been disclosed in the context of the mathematical model which comprises the biochemical model and the pharmacodynamical model. For example, calculating arrangement (110) can be adapted to perform the steps (S9), (S10), (S11) and (S12) as has been described with regard to FIGS. 3a, 3b and 3c. Furthermore, the calculation arrangement (110) may be adapted, if desired, to automatically suggest an application of a coagulant or procoagulant and/or an anti-coagulant to a user.

Additionally such a user interface may be configured to receive coagulation data from different points of time, wherein the user interface may be further configured to display a time-resolved progression of the risk of coagulation and the risk of bleeding of said blood circulation in said graphical representation.

Figure 5:
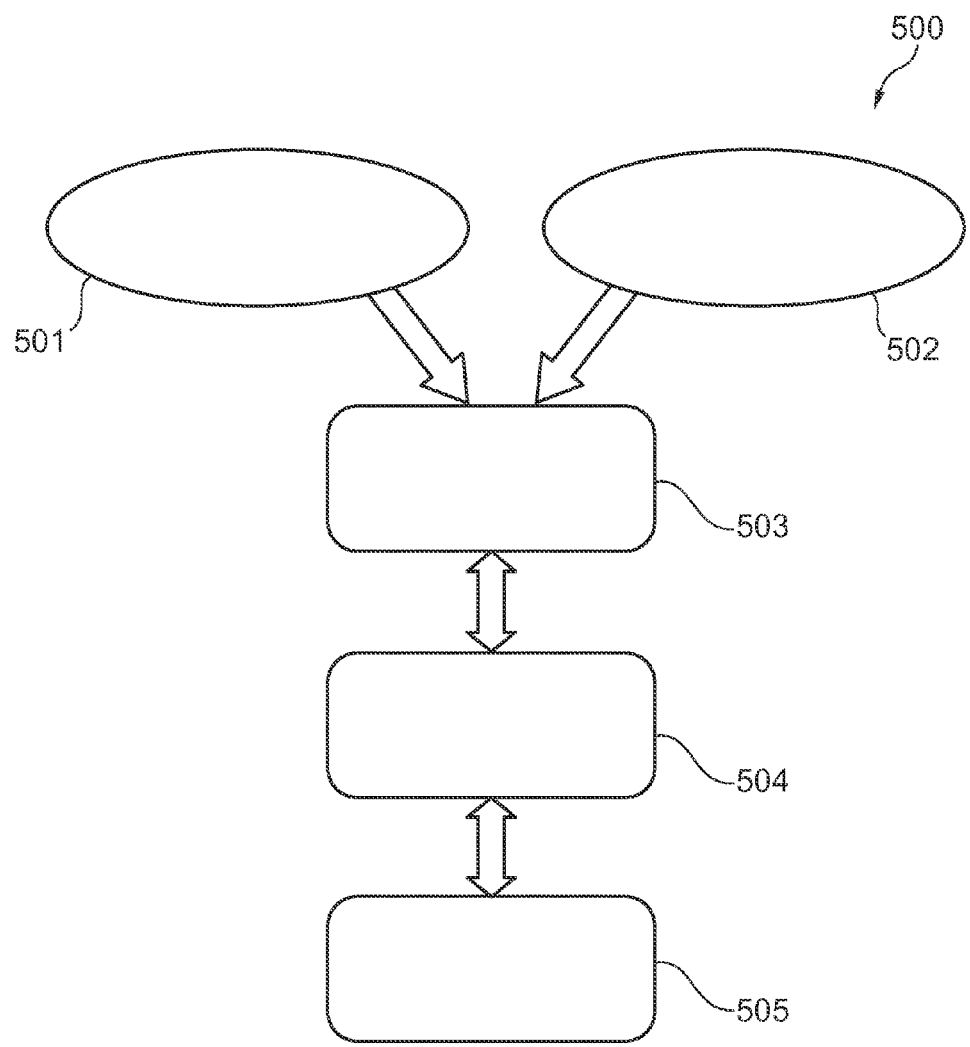
FIG. 5 schematically shows a user interface according to an exemplary embodiment of the invention.

FIG. 5 schematically shows how a user interface (503) might be connected to the other aspects of the invention. User interface (503) might be used in order to receive clinical measurement data (501), for example INR, aPTT, and vitamin K-proteins activity. Such current clinical measurements and previously measured values may be presented by the user interface (503) to the physician. Furthermore, a software layer may be comprised which is depicted by (504). This software layer might be a connector to other IT services in, for example, a hospital IT system. For example a drug ordering system may be connected in such a way to the user interface. The mathematical model, which is used for the calculation of the prediction, is shown in (505). The mathematical model may alternatively be stored in the user interface or also in an external data storage device. (502) depicts that the user or a clinician may input several values which will be explained in detail with regard to the following FIG. 6.

FIG. 6 schematically shows a graphical representation (600) used by a user interface according to an exemplary embodiment of the present invention. The user interface displays an X and Y coordinate system (603) in which the X axis (606) is embodied as an aPTT axis and a Y axis (607) is embodied as an INR axis. However, other test may be used, if desired. In this exemplary representation, five distinct points (609) within that coordinate system are depicted. Between those distinct points in time, the bridge path (610) of the specific patient is shown. Therefore, it can be gathered from the graphical representation (600) how the bleeding and thrombosis risks evolve over time. Furthermore, rectangular areas (608) are displayed to the user in this example which show or depict the region in which a safe haemostatic situation is indicated. This simultaneous display of PTT and INR enables the clinician to monitor the bridge therapy and safely compensate for an incorrect anticoagulation. A solution is offered to the treating physician by means of a graphical user interface as shown in (600). Furthermore, a field for recommended action (604) is presented. Several input possibilities (611) are provided for the user, where he may for example amend the currently provided administration of drugs. By means of button (612) user may chose which potential amendment he wants to have calculated by the underlying mathematical model and the predicted effect of which he wants displayed afterwards on the above zone (603). Furthermore, zone (602) is shown of the optical presentation on which several test values can be entered by the user. These test values (605) may then be submitted to an underlying mathematical model to calculate a prediction.

In zone (601) of the graphical representation individual and/or personal data can be displayed to the user and may also be entered by the user. For example, name, age and weight of the patient may be displayed and/or entered. Or the bridge type may be displayed to the user in order to know which bridging process is going on at the moment. In FIG. 6, the bridge type from VKA to UFH is presented.

Thus, in FIG. 6 the steps of graphically representing the first value as a point on the first axis is depicted which may seen as step S7. Further the step of graphically representing the second value as a point on the second axis is depicted which may be seen as step S8.

The invention claimed is:

1. A method of visualizing a bridge therapy process, the method comprising the steps of:
receiving coagulation data describing a haemostatic situation of a blood circulation of a patient at a computer having a processor and a display, and
displaying, on the display of the computer, the coagulation data to a user by means of a graphical representation, the displaying including:
displaying a first value measured by a first type of blood test, wherein the first value indicates a first effect of a heparin like drug on the haemostatic situation, and simultaneously to the displaying of the first value displaying a second value measured by a second type of blood test, wherein the second value indicates a second effect of a vitamin K antagonist type anticoagulant on the haemostatic situation, and wherein the first and second values describe the haemostatic situation of the blood circulation at a first point in time and are simultaneously displayed as a first point within an X and Y coordinate system having the first value for the X axis and the second value for the Y axis.

2. The method according to claim 1, the displaying of the coagulation data further comprising the steps of:

displaying, on the display of the computer, a third value measured by the first type of blood test, wherein the third value indicates a third effect of a heparin like drug on the haemostatic situation, simultaneously to the displaying of the third value displaying, on the display of the computer, a fourth value measured by the second type of blood test, wherein the fourth value indicates a fourth effect of a vitamin K antagonist type anticoagulant on the haemostatic situation, wherein the third and fourth values describe the haemostatic situation of the blood circulation at a second point in time and are simultaneously displayed as a second point within the X and Y coordinate system having the third value for the X axis and the fourth value for the Y axis.

3. The method according to claim 1, wherein the first and second type of blood test are respectively and independently chosen from the group consisting of activated partial thrombopiastine time (aPTT) test, anti-Factor 10a test, prothrombin time (PT) test, international normalized ratio (INR) test, a test indicating thrombosis or coagulation, a test indicating bleeding or anti-coagulation, a test indicating the haemostatic function.

4. The method according to claim 1, further comprising the step of:

calculating, using the processor of the computer, a prediction of the haemostatic situation of the blood circulation by a mathematical representation of the blood circulation.

5. The method according to claim 1, further comprising the step of:

calculating, using the processor of the computer, a prediction of the haemostatic situation of the blood circulation by combining a biochemical model of the blood circulation and a pharmacodynaniical model of the blood circulation.

6. The method according to claim 5, further comprising the steps of:

calculating, using the processor of the computer, an effect of an anticoagulant drug during a predetermined time by using the pharmacodynamical model, to generate a calculated pharmacodynamical effect.

7. The method according to claim 6, the method further comprising the steps of:

calculating, using the processor of the computer, a coagulation effect and/or a fibrin polymerization effect with the biochemical model based on the calculated pharmacodynamical effect, and displaying, on the display of the computer, a prediction value of the haemostatic situation, wherein the prediction value is based on at least one of the calculated pharmacodynamical effect, the calculated coagulation effect, and the calculated fibrin polymerization effect.

8. The method according to claim 1, the method further comprising the step of:

automatically suggesting an application of a coagulant and/or an anti-coagulant.

9. The method according to claim 8, wherein the step of automatically suggesting an application of a coagulant and/or an anti-coagulant is based on a calculated progression of the haemostatic situation.

10. The method of claim 1 further comprising the step of:

displaying a rectangle in the X and Y coordinate system depicting a region in which a safe haemostatic situation is indicated.

11. A user interface device for visualizing a bridge therapy process, the user interface comprising:

a user interface configured to receive coagulation data describing a haemostatic situation of a blood circulation of a patient, a display configured to display the haemostatic situation of said blood circulation including:

displaying a first value measured by a first type of blood test, wherein the first value indicates a first effect of a heparin like drug on the haemostatic situation, and simultaneously displaying a second value measured by a second type of blood test, wherein the second value indicates a second effect of a vitamin K antagonist type anticoagulant on the haemostatic situation;

wherein the first and second values describe the haemostatic situation of the blood circulation at a first point in time; and wherein the first and second values are simultaneously displayed as the first point within a two-dimensional coordinate system having an axis for the first type of blood test and a different axis for the second type of blood test.

12. The user interface device according to claim 11 wherein the user interface is configured to display a time progression of the haemostatic situation of said blood circulation by further:

displaying a third value measured by the first type of blood test, wherein the third value indicates a third effect of a heparin like drug on the haemostatic situation at a second point in time, and displaying a fourth value measured by the second type of blood test simultaneously to the first, second and third value, wherein the fourth value indicates a fourth effect of a vitamin K antagonist type anticoagulant on the haemostatic situation at the second point in time, and wherein the third and fourth values describe the haemostatic situation of the blood circulation at the second point in time.

13. The user interface device according to claim 11, further comprising:

a computer processor configured to calculate a prediction of the haemostatic situation of the blood circulation by using mathematical representation of the blood circulation or by a combining a biochemical model of the blood, circulation and a pharmacodynamical model of the blood circulation.

14. The user interface device according to claim 11, wherein the computer processor is configured to:

calculate an effect of an anticoagulant drug during a predetermined time by using the pharmacodynamical model, generate a calculated pharmacodynamical effect, and use the calculated pharmacodynamical effect as an input for the biochemical model.

15. The user interface device of claim 11 wherein the display is configured to further display a rectangle in the two-dimensional coordinate system depicting a region in which a safe haemostatic situation is indicated.

16. A non-transitory computer readable medium in which a program element for visualizing a bridge therapy process is stored, which, when being executed by a computer including a processor and a display performs a method including:
  receiving coagulation data describing a haemostatic situation of a blood circulation including at least:
    a first value measured at a first point in time by a first type of blood test that indicates an effect of a heparin like drug on the haemostatic situation, and
    a second value measured at the first point in time by a second type of blood test that indicates an effect of a vitamin K antagonist type anticoagulant on the haemostatic situation,
  displaying, on the display, a two-dimensional coordinate system having a first axis representing the first type of blood test and a second axis representing the second type of blood test, and
  plotting a point in the two-dimensional coordinate system representing the effect at the first point in time of both the heparin like drug and the vitamin K antagonist type anticoagulant, the plotted point having the first value on the first axis and the second value on the second axis.

* * * * *